US011821310B2

(12) United States Patent
Kallehbasti et al.

(10) Patent No.: US 11,821,310 B2
(45) Date of Patent: Nov. 21, 2023

(54) DRILLING FLUID CONTAMINATION DETERMINATION FOR DOWNHOLE FLUID SAMPLING TOOL

(71) Applicant: Halliburton Energy Services, Inc., Houston, TX (US)

(72) Inventors: Mehdi Alipour Kallehbasti, Humble, TX (US); Peter Ojo Olapade, Richmond, TX (US); Bin Dai, Spring, TX (US); Christopher Michael Jones, Katy, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 616 days.

(21) Appl. No.: 16/610,786

(22) PCT Filed: Nov. 30, 2018

(86) PCT No.: PCT/US2018/063260
§ 371 (c)(1),
(2) Date: Nov. 4, 2019

(87) PCT Pub. No.: WO2020/112135
PCT Pub. Date: Jun. 4, 2020

(65) Prior Publication Data
US 2021/0047924 A1 Feb. 18, 2021

(51) Int. Cl.
*E21B 49/08* (2006.01)
*G01N 33/28* (2006.01)
(Continued)

(52) U.S. Cl.
CPC ........ *E21B 49/0875* (2020.05); *E21B 49/086* (2013.01); *G01N 21/31* (2013.01);
(Continued)

(58) Field of Classification Search
CPC .... E21B 49/0875; E21B 49/086; E21B 49/10; E21B 49/08; G01N 21/31;
(Continued)

(56) References Cited

U.S. PATENT DOCUMENTS

| 7,788,972 B2 * | 9/2010 | Terabayashi | .......... E21B 49/081 |
| | | | 73/152.27 |
| 10,416,349 B2 * | 9/2019 | Bang | ...................... G01V 99/00 |

(Continued)

FOREIGN PATENT DOCUMENTS

| WO | WO-2015039090 A1 * | 3/2015 | ............. E21B 49/00 |
| WO | 2018031021 | 2/2018 | |

(Continued)

OTHER PUBLICATIONS

International Search Report and Written Opinion for PCT/US2018/063260 dated Aug. 16, 2019.

(Continued)

*Primary Examiner* — Rebecca C Bryant
*Assistant Examiner* — Christopher J Gassen
(74) *Attorney, Agent, or Firm* — John Wustenberg; C. Tumey Law Group PLLC

(57) ABSTRACT

A method and a system for determining fluid contamination. The method may comprise monitoring a fluid sample, wherein the fluid sample comprises a reservoir fluid contaminated with a well fluid, and obtaining input parameters, wherein the input parameters comprise fluid properties obtained from measurement of the fluid sample and mud filtrate composition. The method may further comprise representing a mud composition as a Gaussian distribution, selecting a plurality of input data during a pumpout, determining calculated fluid properties of the reservoir fluid using an equation of state filtrate analysis, and further obtaining updated vales of iterative parameters for use in a mole (Continued)

fraction distribution function. The system may comprise a downhole fluid sampling tool operable to obtain fluid samples of a reservoir fluid contaminated with a well fluid while the downhole fluid sampling tool is disposed in a wellbore, and a processor.

20 Claims, 9 Drawing Sheets

(51) Int. Cl.
 *G01N 21/88* (2006.01)
 *G01N 21/31* (2006.01)
 *G01N 21/94* (2006.01)

(52) U.S. Cl.
 CPC ......... *G01N 21/8851* (2013.01); *G01N 21/94* (2013.01); *G01N 33/2823* (2013.01); *G01N 2021/8887* (2013.01)

(58) Field of Classification Search
 CPC ............... G01N 21/8851; G01N 21/94; G01N 33/2823; G01N 2021/8887
 See application file for complete search history.

(56) References Cited

U.S. PATENT DOCUMENTS

| | | | | |
|---|---|---|---|---|
| 10,859,730 | B2* | 12/2020 | Raman | G06N 3/08 |
| 2003/0223068 | A1* | 12/2003 | DiFoggio | G01J 3/26 |
| | | | | 356/419 |
| 2004/0104341 | A1* | 6/2004 | Betancourt | G01N 1/12 |
| | | | | 250/255 |
| 2008/0141767 | A1* | 6/2008 | Raghuraman | G01N 33/2823 |
| | | | | 73/152.55 |
| 2013/0311099 | A1* | 11/2013 | Eyuboglu | E21B 49/081 |
| | | | | 702/11 |
| 2016/0090836 | A1* | 3/2016 | Wang | E21B 49/08 |
| | | | | 702/12 |
| 2016/0186559 | A1* | 6/2016 | Wang | E21B 49/10 |
| | | | | 702/6 |
| 2016/0186562 | A1* | 6/2016 | Lee | G06Q 50/02 |
| | | | | 702/6 |
| 2016/0216404 | A1* | 7/2016 | Kristensen | E21B 49/10 |

FOREIGN PATENT DOCUMENTS

| | | |
|---|---|---|
| WO | 2018144606 | 8/2018 |
| WO | 2020/005238 | 1/2020 |

OTHER PUBLICATIONS

P. Sah et al. (2012) Equation-of-state modeling for reservoir-fluid samples contaminated by oil-based drilling mud using contaminated-fluid pressure/volume/temperature data.

Julian Zuo et at. (2011) Equation-of-state-based downhold fluid characterization.

* cited by examiner

DRILLING FLUID CONTAMINATION DETERMINATION FOR DOWNHOLE FLUID SAMPLING TOOL

BACKGROUND

During oil and gas exploration, many types of information may be collected and analyzed. The information may be used to determine the quantity and quality of hydrocarbons in a reservoir and to develop or modify strategies for hydrocarbon production. For instance, the information may be used for reservoir evaluation, flow assurance, reservoir stimulation, facility enhancement, production enhancement strategies, and reserve estimation. One technique for collecting relevant information involves obtaining and analyzing fluid samples from a reservoir of interest. There are a variety of different tools that may be used to obtain the fluid sample. The fluid sample may then be analyzed to determine fluid properties, including, without limitation, component concentrations, plus fraction molecular weight, gas-oil ratios, bubble point, dew point, phase envelope, viscosity, combinations thereof, or the like. Conventional analysis has required transfer of the fluid samples to a laboratory for analysis. Downhole analysis of the fluid sample may also be used to provide real-time fluid properties, thus avoiding delays associated with laboratory analysis.

Accurate determination of fluid properties may be problematic as the fluid sample may often be contaminated with drilling fluids. Fluid samples with levels of drilling fluid contamination may result in non-representative fluids and measured properties. Techniques to determine drilling fluid contamination may include use of pumpout curves, such as density, gas-to-oil ratio and resistivity, among other properties of the fluids. However, determination of drilling fluid contamination using these techniques may be limited, for example, due to lack of significant decrease of the property value, non-linear behavior or properties to contamination levels, and unreliable property measurements. To reduce drilling fluid contamination, longer pumpout time may be required, which can lead to loss of rig time and increase risk of stuck tools, among other problems.

BRIEF DESCRIPTION OF THE DRAWINGS

These drawings illustrate certain aspects of some of the embodiments of the present invention, and should not be used to limit or define the invention.

DETAILED DESCRIPTION

Disclosed herein are methods and systems for subterranean operations and, in some embodiments, methods and systems for determination of contamination level of a fluid sample from a downhole fluid sampling tool. Knowledge of the fluid contamination (e.g., oil based drilling fluid contamination) may then allow right time of sampling and determination of fluid properties of the reservoir fluid, even though the fluid sample was contaminated with well fluid, such as a drilling fluid or other well fluid introduced from the surface.

For example, reservoir fluid sample with oil based mud contamination (OBM) greater than 10% for oil and 3% for condensate may be considered unusable because the OBM alters the properties of the fluid and the altered properties are not representative of the properties of the clean reservoir fluid. Samples with high OBM contamination are thus a loss of investment. It is therefore important to ascertain that the contamination level is acceptably low before samples are collected. Most of the existing methods of estimating formation contamination level rely on trend fitting and consequently suffer from tool drifting and dependence of end member filtrate value. A new method may be beneficial that uses equation of state, inherent geochemistry of the formation fluid and empirical correlation based on a data from a single pumpout time. However, new methods may also need mud composition which may not be available at the time of drilling. Thus, to use an equation of state approach when the mud composition is not available, method for estimating the mud composition must be developed. By observing various mud compositions, one may estimate the mean and the standard deviation of the mud composition. It may also be known that at various pumpout times, even though the contamination levels different, the formation fluid and the filtrate composition may be nearly identical. It may be therefore necessary to extend the original equation of state approach to be able to estimate the mud composition when it may not be available during pumpout.

Figure 1:
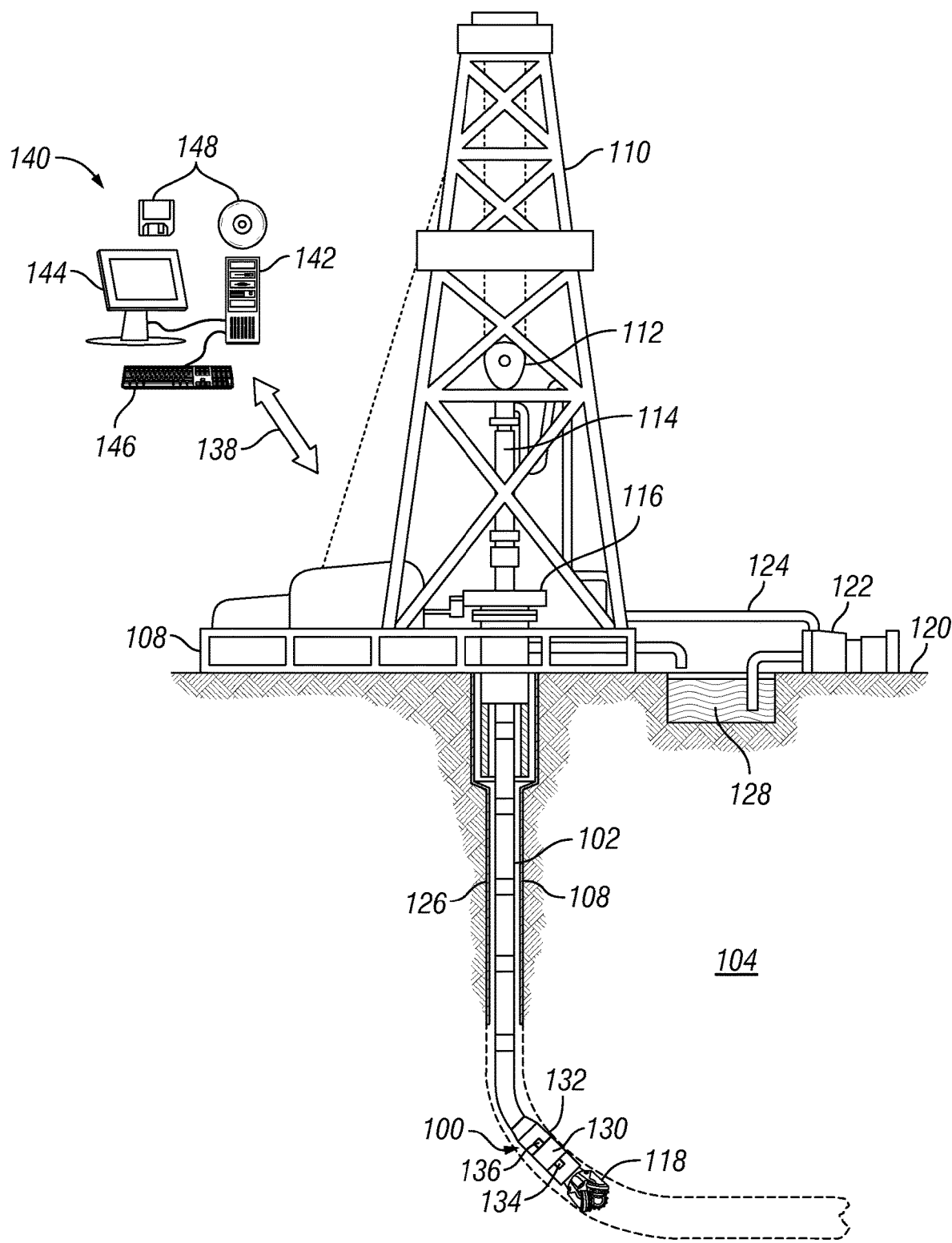
FIG. 1 is a schematic diagram of an example downhole fluid sampling tool on a drill string.

FIG. 1 is a schematic diagram is shown of downhole fluid sampling tool 100 disposed on a drill string 102. The downhole fluid sampling tool 100 may be used to obtain a fluid sample, for example, a fluid sample of a reservoir fluid from subterranean formation 104. The reservoir fluid may be contaminated with well fluid (e.g., drilling fluid) from wellbore 106. As described herein, the fluid sample may be analyzed to determine fluid contamination and other fluid properties of the reservoir fluid. As illustrated, a wellbore 106 may extend through subterranean formation 104. While the wellbore 106 is shown extending generally vertically into the subterranean formation 104, the principles described herein are also applicable to wellbores that extend at an angle through the subterranean formation 104, such as horizontal and slanted wellbores. For example, although FIG. 1 shows a vertical or low inclination angle well, high inclination angle or horizontal placement of the well and equipment is also possible. It should further be noted that while FIG. 1 generally depicts a land-based operation, those skilled in the art will readily recognize that the principles described herein are equally applicable to subsea operations that employ floating or sea-based platforms and rigs, without departing from the scope of the disclosure.

As illustrated, a drilling platform 108 may support a derrick 110 having a traveling block 112 for raising and lowering drill string 102. Drill string 102 may include, but is not limited to, drill pipe and coiled tubing, as generally known to those skilled in the art. A kelly 114 may support drill string 102 as it may be lowered through a rotary table 116. A drill bit 118 may be attached to the distal end of drill string 102 and may be driven either by a downhole motor and/or via rotation of drill string 102 from the surface 120. Without limitation, drill bit 118 may include, roller cone bits, PDC bits, natural diamond bits, any hole openers, reamers, coring bits, and the like. As drill bit 118 rotates, it may create and extend wellbore 106 that penetrates various subterranean formations 104. A pump 122 may circulate drilling fluid through a feed pipe 124 to kelly 114, downhole through interior of drill string 102, through orifices in drill bit 118, back to surface 120 via annulus 126 surrounding drill string 102, and into a retention pit 128.

Drill bit 118 may be just one piece of a downhole assembly that may include one or more drill collars 130 and downhole fluid sampling tool 100. Downhole fluid sampling tool 100, which may be built into the drill collars 130) may gather measurements and fluid samples as described herein. One or more of the drill collars 130 may form a tool body 132, which may be elongated as shown on FIG. 1. Tool body 132 may be any suitable material, including without limitation titanium, stainless steel, alloys, plastic, combinations thereof, and the like. Downhole fluid sampling tool 100 may further include one or more sensors 134 for measuring properties of the fluid sample, reservoir fluid, wellbore 106, subterranean formation 104, or the like. The downhole fluid sampling tool 100 may be used to collect a fluid sample from subterranean formation 104. As previously described, the fluid sample may comprise a reservoir fluid, which may be contaminated with a well fluid. The downhole fluid sampling tool 100 may obtain and separately store different fluid samples from subterranean formation 104. However, storing of the fluid samples in the downhole fluid sampling tool 100 may be based on the determination of the fluid contamination. For example, if the fluid contamination exceeds a tolerance, then the fluid sample may not be stored. If the fluid contamination is within a tolerance, then the fluid sample may be stored in the downhole fluid sampling tool 100.

The downhole fluid sampling tool 100 may further include a fluid analysis module 136. In examples, the fluid analysis module 136 may comprise an optical sensor that may continuously monitor a reservoir fluid. The fluid analysis module 136 may be operable to derive properties and characterize the fluid sample. By way of example, the fluid analysis module 136 may measure absorption spectra and translate such measurements into component concentrations of the fluid sample, which may be lumped component concentrations, as described above. The fluid analysis module 136 may also measure gas-to-oil ratio, live fluid density, live fluid viscosity, formation pressure, and formation temperature. The fluid analysis module 136 may also be operable to determine fluid contamination of the fluid sample. The fluid analysis module 136 include any instrumentality or aggregate of instrumentalities operable to compute, classify, process, transmit, receive, retrieve, originate, switch, store, display, manifest, detect, record, reproduce, handle, or utilize any form of information, intelligence, or data for business, scientific, control, or other purposes. For example, fluid analysis module 136 may include random access memory (RAM), one or more processing units, such as a central processing unit (CPU), or hardware or software control logic, ROM, and/or other types of nonvolatile memory.

Any suitable technique may be used for transmitting signals from the downhole fluid sampling tool 100 to the surface 120. As illustrated, a communication link 138 (which may be wired or wireless, for example) may be provided that may transmit data from downhole fluid sampling tool 100 to an information handling system 140 at surface 120. Information handling system 140 may include a processing unit 142, a monitor 144, an input device 146 (e.g., keyboard, mouse, etc.), and/or computer media 148 (e.g., optical disks, magnetic disks) that can store code representative of the methods described herein. The information handling system 140 may act as a data acquisition system and possibly a data processing system that analyzes information from downhole fluid sampling tool 100. For example, information handling system 140 may process the information from downhole fluid sampling tool 100 for determination of fluid contamination. The information handling system 140 may also determine additional properties of the fluid sample (or reservoir fluid), such as component concentrations, pressure-volume-temperature properties (e.g., bubble point, phase envelop prediction, etc.) based on the fluid characterization. This processing may occur at surface 120 in real-time. Alternatively, the processing may occur at surface 120 or another location after recovery of downhole fluid sampling tool 100 from wellbore 106. Alternatively, the processing may be performed by an information handling system in wellbore 106, such as fluid analysis module 136. The resultant fluid contamination and fluid properties may then be transmitted to surface 120, for example, in real-time.

Figure 2:
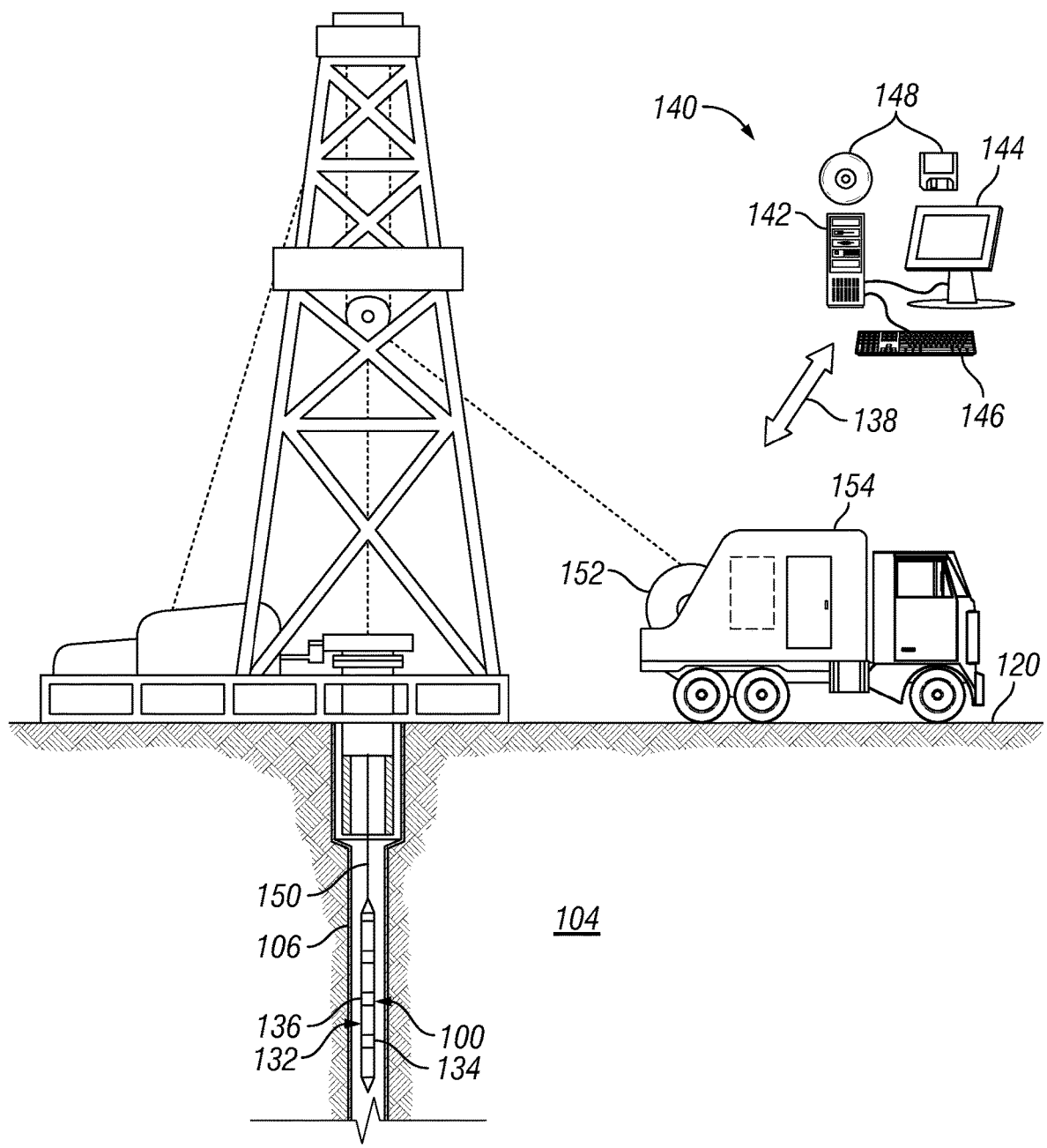
FIG. 2 is a schematic diagram of an example downhole fluid sampling tool on a wireline.

Referring now to FIG. 2, a schematic diagram is shown of downhole fluid sampling tool 100 on a wireline 150. As illustrated, wellbore 106 may extend through subterranean formation 104. Downhole fluid sampling tool 100 may be similar in configuration and operation to downhole fluid sampling tool 100 shown on FIG. 1 except that FIG. 2 shows downhole fluid sampling tool 100 disposed on wireline 150. It should be noted that while FIG. 2 generally depicts a land-based drilling system, those skilled in the art will readily recognize that the principles described herein are equally applicable to subsea drilling operations that employ floating or sea-based platforms and rigs, without departing from the scope of the disclosure.

As illustrated, a hoist 152 may be used to run downhole fluid sampling tool 100 into wellbore 106. Hoist 152 may be disposed on a recovery vehicle 154. Hoist 152 may be used, for example, to raise and lower wireline 150 in wellbore 106. While hoist 152 is shown on recovery vehicle 154, it should be understood that wireline 150 may alternatively be disposed from a hoist 152 that is installed at surface 120 instead of being located on recovery vehicle 154. Downhole fluid sampling tool 100 may be suspended in wellbore 106 on wireline 150. Other conveyance types may be used for conveying downhole fluid sampling tool 100 into wellbore 106, including coiled tubing and wired drill pipe, for example. Downhole fluid sampling tool 100 may comprise a tool body 132, which may be elongated as shown on FIG. 1. Tool body 132 may be any suitable material, including without limitation titanium, stainless steel, alloys, plastic, combinations thereof, and the like. Downhole fluid sampling tool 100 may further include one or more sensors 134 for measuring properties of the fluid sample, reservoir fluid, wellbore 106, subterranean formation 104, or the like. The downhole fluid sampling tool 100 may also include a fluid analysis module 136, which may be operable to process information regarding fluid sample, as described above with respect to FIG. 1. The downhole fluid sampling tool 100 may be used to collect fluid samples from subterranean formation 104. The downhole fluid sampling tool 100 may obtain and separately store different fluid samples from subterranean formation 104.

As previously described, information from downhole fluid sampling tool 100 may be transmitted to an information handling system 140, which may be located at surface 120. As illustrated, communication link 138 (which may be wired or wireless, for example) may be provided that may transmit data from downhole fluid sampling tool 100 to an information handling system 140 at surface 120. Information handling system 140 may include a processing unit 142, a monitor 144, an input device 146 (e.g., keyboard, mouse, etc.), and/or computer media 148 (e.g., optical disks, magnetic disks) that can store code representative of the methods described herein. In addition to, or in place of processing at surface 120, processing may occur downhole (e.g., fluid analysis module 136).

Figure 3:
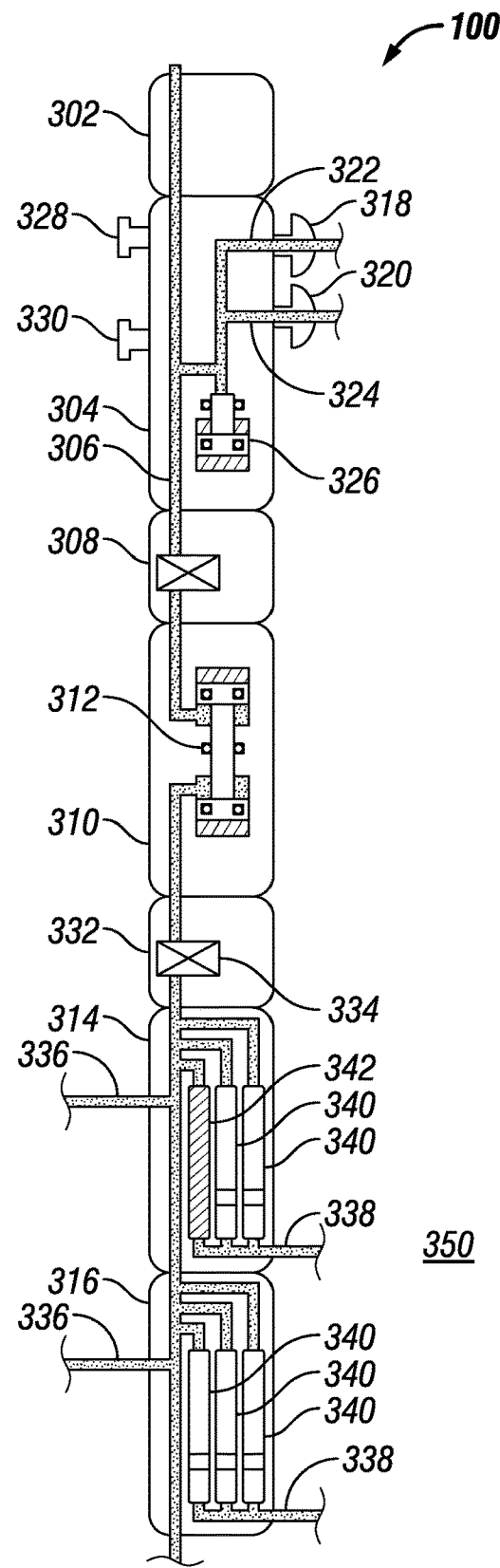
FIG. 3 is a flow chart of an example method for determining fluid contamination of a fluid sample of a reservoir fluid.

FIG. 3 is a schematic example of downhole fluid sampling tool 100. In examples, downhole fluid sampling tool 100 includes a power telemetry section 302 through which the tool communicates with other actuators and sensors in drill string 102 or conveyance (e.g., referring to FIGS. 1 and 2), the drill string's telemetry section 302, and/or directly with a surface telemetry system (not illustrated). In examples, power telemetry section 302 may also be a port through which the various actuators (e.g. valves) and sensors (e.g., temperature and pressure sensors) in the downhole fluid sampling tool 100 may be controlled and monitored. In examples, power telemetry section 302 includes a computer that exercises the control and monitoring function. In one embodiment, the control and monitoring function is performed by a computer in another part of the drill string or wireline tool (not shown) or by information handling system 140 on surface 120 (e.g., referring to FIGS. 1 and 2).

In examples, downhole fluid sampling tool 100 includes a dual probe section 304, which extracts fluid from the reservoir and delivers it to a channel 306 that extends from one end of downhole fluid sampling tool 100 to the other. Without limitation, dual probe section 304 includes two probes 318, 320 which may extend from downhole fluid sampling tool 100 and press against the inner wall of wellbore 106 (e.g., referring to FIGS. 1 and 2). Probe channels 322, 324 may connect probes 318, 320 to channel 306. The high-volume bidirectional pump 312 may be used to pump fluids from the reservoir, through probe channels 322, 324 and to channel 306. Alternatively, a low volume pump 326 may be used for this purpose. Two standoffs or stabilizers 328, 330 hold downhole fluid sampling tool 100 in place as probes 318, 320 press against the wall of wellbore 106. In examples, probes 318, 320 and stabilizers 328, 330 may be retracted when downhole fluid sampling tool 100 may be in motion and probes 318, 320 and stabilizers 328, 330 may be extended to sample the formation fluids at any suitable location in wellbore 104. Other probe sections include focused sampling probes, oval probes, or packers.

In examples, channel 306 may be connected to other tools disposed on drill string 102 or conveyance (e.g., referring to FIGS. 1 and 2). In examples, downhole fluid sampling tool 100 may also include a quartz gauge section 308, which may include sensors to allow measurement of properties, such as temperature and pressure, of fluid in channel 306. Additionally, downhole fluid sampling tool 100 may include a flow-control pump-out section 310, which may include a high-volume bidirectional pump 312 for pumping fluid through channel 306. In examples, downhole fluid sampling tool 100 may include two multi-chamber sections 314, 316, referred to collectively as multi-chamber sections 314, 316 or individually as first multi-chamber section 314 and second multi-chamber section 316, respectively.

In examples, multi-chamber sections 314, 316 may be separated from flow-control pump-out section 310 by sensor section 332, which may house at least one sensor 334. Sensor 334 may be displaced within sensor section 332 in-line with channel 306 to be a "flow through" sensor. In alternate examples, sensor 334 may be connected to channel 306 via an offshoot of channel 306. Without limitation, sensor 334 may include optical sensors, acoustic sensors, electromagnetic sensors, conductivity sensors, resistivity sensors, selective electrodes, density sensors, mass sensors, thermal sensors, chromatography sensors, viscosity sensors, bubble point sensors, fluid compressibility sensors, flow rate sensors, microfluidic sensors, selective electrodes such as ion selective electrodes, and/or combinations thereof. In examples, sensor 334 may operate and/or function to measure drilling fluid filtrate, discussed further below.

Additionally, multi-chamber section 314, 316 may comprise access channel 336 and chamber access channel 338. Without limitation, access channel 336 and chamber access channel 338 may operate and function to either allow a solids-containing fluid (e.g., mud) disposed in wellbore 106 in or provide a path for removing fluid from downhole fluid sampling tool 100 into wellbore 106. As illustrated, multi-chamber section 314, 316 may comprise a plurality of chambers 340. Chambers 340 may be sampling chamber that may be used to sample wellbore fluids, formation fluids, and/or the like during measurement operations. As illustrated in FIG. 3, in examples, at least one chamber 340, may be a filter 342. Filter 342 may be disposed in any chamber 340 and is not limited to the illustration in FIG. 3. Additionally, there may be any number of filters 342 disposed in any number of multi-chamber sections 314, 316.

During measurement operations, it may be beneficial to determine drilling fluid filtrate before and/or after a pumpout. A pumpout may be an operation where at least a portion of a solids-containing fluid (e.g., drilling fluid, mud, etc.) may move through downhole fluid sampling tool 100 until substantially increasing concentrations of formation fluids enter downhole fluid sampling tool 100. However, before pumpout, it may be beneficial to measure drilling fluid filtrate with sensor section 332 utilizing sensor 334. To perform this operation, high-volume bidirectional pump 312 may pull drilling fluid 350 from wellbore 106 (e.g., referring to FIGS. 1 and 2) into downhole fluid sampling tool 100. For this operation, chamber valve 520 (e.g., referring to FIG. 3) may be open, which may allow high-volume bidirectional pump 312 to draw drilling fluid 350 through chamber access channel 338. Drilling fluid 350 may traverse through chamber access channel 338 to filter 342. Drilling fluid 350 may move across filter 342 and filter 342 may remove particulate manner in drilling fluid 350. As drilling fluid 350 traverses through filter 342 it may become drilling fluid filtrate. The drilling fluid filtrate may pass through first chamber valve 520 and into channel 306 toward high-volume bidirectional pump 312. As the drilling fluid filtrate moves toward high-volume bidirectional pump 312, the drilling fluid filtrate may move into sensor section 332. Once the drilling fluid filtrate has moved into sensor section 332 high-volume bidirectional pump 312 may stop. This may allow the drilling fluid filtrate to be measured by sensor 334 within sensor section 332. Without limitation, any suitable properties of the drilling fluid filtrate may be measured. These measurements may allow an operator to calibrate sensor 334 for quality control. In examples, these measurements may be used to constrain the sensor signatures during contamination, normalize measurements of two or more sensors 334, and or correlate two or more dissimilar sensors 334.

Figure 4:
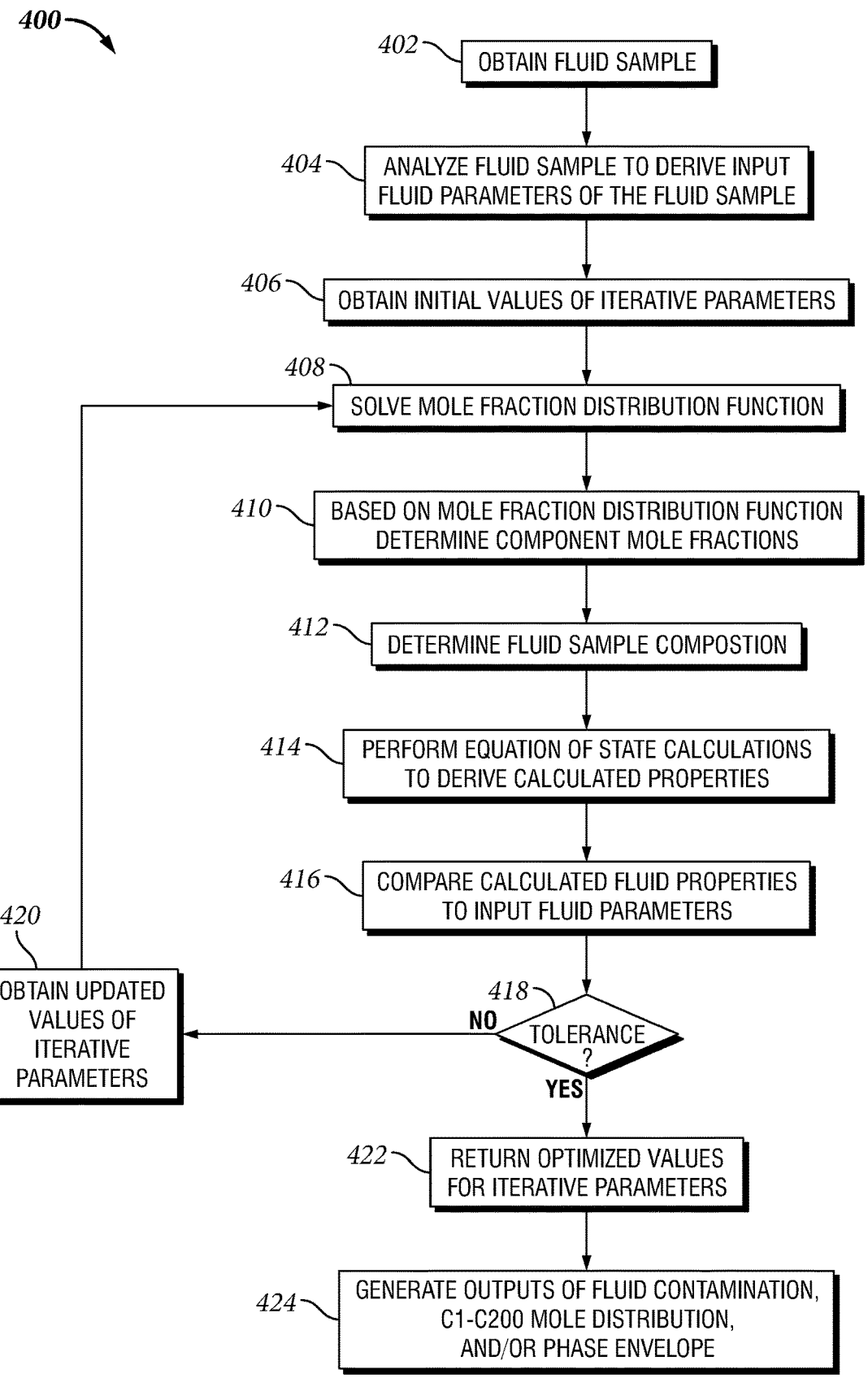
FIG. 4 is a chart illustrating parameterized mud composition for various number of pumpout data.

FIG. 4 shows a flow chart of an example of a method 400 for determining fluid contamination. Method 400 may be implemented using the systems implemented on FIGS. 1 and 2, for example, to determine fluid contamination (e.g., drilling fluid contamination) of a fluid sample. In examples, 400 may be implemented at surface 120 or in wellbore 106. By way of example, fluid analysis module 136 of downhole fluid sampling tool 100 may include a processing unit (e.g., a microprocessor, etc.) that can be operable to implement one or more of the method steps of method 400. By way of further example, information handling system 140 may also include a processing unit 142 (e.g., a microprocessor, etc.) that can be operable to implement one or more of the method steps of method 400. As will be appreciated, processing may occur either in wellbore 106, at surface 120, at a remote location, or a combination of these locations.

In step 402, a fluid sample may be obtained. The fluid sample may be a fluid sample from a reservoir of interest, for example, from subterranean formation 104 shown on FIGS. 1 and 2. Any suitable technique may be used to obtain fluid sample. As described previously, downhole fluid sampling tool 100 may be used to collect fluid sample on a drill string 102 (e.g., FIG. 1) or on a wireline 150 (e.g., FIG. 2), for example. For example, downhole fluid sampling tool 100 may be operated to obtain a fluid sample. The fluid sample may be contaminated with a well fluid, such as drilled fluid. The fluid sample may be obtained at formation temperature and pressure. It should be understood that downhole fluid sampling tool 100 is merely illustrative of one example apparatus that may be used in obtaining a fluid sample and those of ordinary skill in the art should be able to select an appropriate apparatus and associated methodology to obtain a fluid sample. The fluid sample need not necessarily be collected downhole. By way of example, the techniques described herein may be used to characterize the fluid sample of a produced fluid that may be obtained at surface 120. After fluid sample is obtained, subsequent processing steps (e.g., steps 404 to 424) may occur at surface 120 or in wellbore 106. Alternatively, fluid sample may be transferred to a remote location for one or more of the subsequent processing steps.

In step 404, the fluid sample may be analyzed to derive input parameters that characterize the fluid sample. Without limitation, the input parameters may be obtained from measurements of the fluid sample. The measurements may be performed in wellbore 106, at surface 120, or at a remote location. Downhole fluid sampling tool 100 or other suitable formation evaluation tools may be used to analyze the fluid sample. Any measuring instrument capable of producing a measurable response to the change of the fluid property may be used. The measuring instrument may contain a detector and/or sensor detecting, for example, density, resistivity/conductivity, viscosity, chromatography, radioactivity, dielectric constant, optical density, magnetic resonance, weight, acoustic impedance, acoustic velocity, optical response, diffusion coefficients, molecular weight, refractive index at various wavelengths, and combinations thereof. One or more sensors or detectors (e.g. sensor 134 of downhole fluid sampling tool 100 shown on FIG. 1) may be used in the measuring instrument.

The input parameters of the fluid sample that may be derived may include fluid properties that may be obtained from measurements of the fluid sample, including, without limitation, one or more of component concentrations (e.g., weight %, etc.), gas-to-oil ratio, live oil density (or dead oil density) and bubble point. Additional fluid properties that may be derived may include one or more of volume fraction of water, API gravity, live oil viscosity, formation temperature, or formation pressure, among others. The component concentrations obtained from these measurements may typically be a lumped component concentration with concentration of heavier hydrocarbons lumped together. By way of example, the component concentration may be provided showing fractions of carbon dioxide ($CO_2$), methane ($CH_4$), ethane ($C_2H_6$), propane ($C_3H_8$), butane ($C_4H_{10}$), pentane ($C_5H_{12}$), and the C6+ group. The C6+ group may include the concentration of all hydrocarbons with six or more carbon atoms lumped into a single component concentration. In some instances, the C5 hydrocarbons may not be separately reported, with the C5+ hydrocarbon group lumped into a single component concentration. Moreover, some of the lower hydrocarbons, such as the C3, C4, or C5 hydrocarbons may also be grouped and reported together, for example, C3-C4 hydrocarbon group, C3-C5 hydrocarbon group, and/or C4-C5 hydrocarbon group. These concentrations may be provided as weight or mole percentages. "Live oil" typically refers to an oil at reservoir conditions. A fluid sample at reservoir conditions may be referred as "live oil." The live oil density of the fluid sample may be obtained from measurements at reservoir conditions. Without limitation, the live oil density may be obtained using a density sensor, for example, on downhole fluid sampling tool 100. The bubble point may include the temperature and pressure at which the first bubble of gas comes out of the fluid sample. Without limitation, the bubble point may be obtained either from measurement or derived from empirical correlation. Without limitation, the gas-to-oil ratio may be obtained by measuring the quantity of vapor component and liquid components of crude oil using near infrared absorption peaks. The ratio of methane to the oil peak on a single phase live crude oil may be directly related to gas-to-oil ratio.

Additional input parameters may also include mud filtrate composition. The term "mud filtrate" typically refers to the liquid part of a drilling fluid, for example, that passes through filter cake. Any suitable method may be used to derive the mud filtrate composition, including a mud log.

In step 406, initial values for iterative parameters may be determined. The iterative parameters may be determined based on one or more of the input parameters. The iterative parameters may be optimized by iteration through method 400, for example, steps 408 to 420. The iterative parameters may include one or more of molecular weight of C6+ components ($\lambda 1$), density of C36+ components ($\lambda 2$), and/or fluid contamination ($\lambda 3$). The molecular weight of C6+ components ($\lambda 1$) and density of C36+ components ($\lambda 2$) may be for a reservoir fluid that is considered clean without any contaminants. The molecular weight of C6+ components ($\lambda 1$), density of C36+ components ($\lambda 2$), and fluid contamination ($\lambda 3$) may be unknown variable whose value may be optimized using method 400. Using the optimized values, component concentrations of the reservoir fluid, including a deplumped component concentration, may be determined. The initial values for molecular weight of C6+ components ($\lambda 1$) and density of C36+ components ($\lambda 2$), and fluid contamination ($\lambda 3$) may derived using the input parameters obtained in step 404 from analysis of fluid sample.

Figure 5:
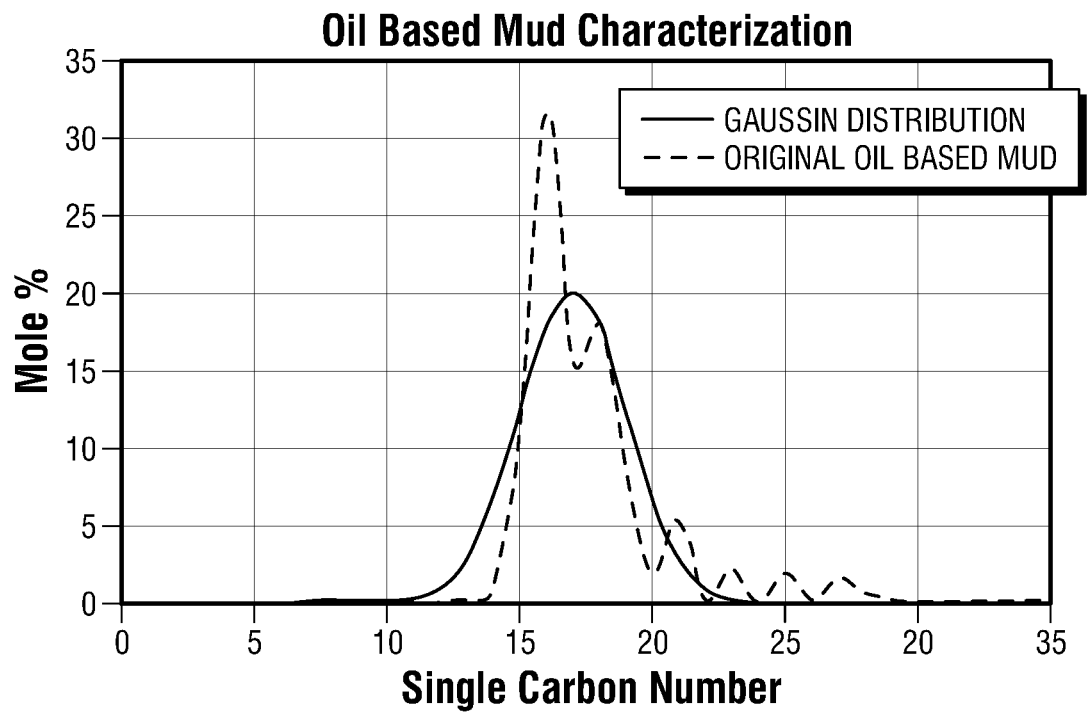
FIG. 5 is a chart illustrating predicted contamination level with eight pump out data points vs observed contamination level.
Figure 6:
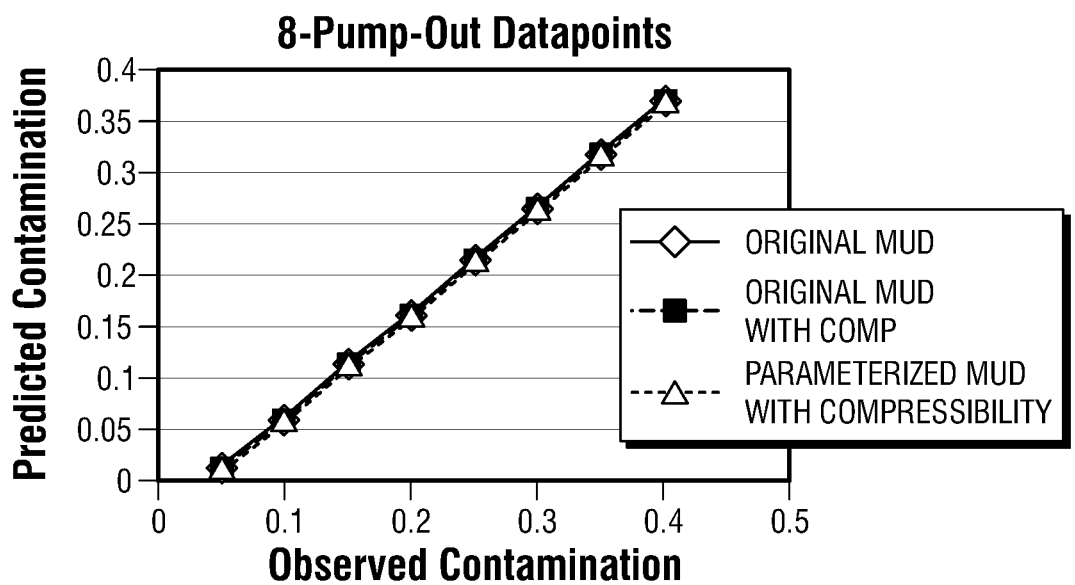
FIG. 6 illustrates a workflow approach for spectral data reconstruction.

Next, a mole fraction distribution function may be used to determine component mole fractions of the reservoir fluid. In step 408, the mole fraction distribution function may be solved and, in step 410, the component mole fractions of the reservoir fluid may be determined based on the mole fraction distribution function. The mole fraction distribution function may characterize reservoir fluid as a function of mole fraction of different components of the fluid. FIG. 5 shows a live oil single carbon number mole fraction distribution for a number of reservoir fluids. As illustrated, the mole fraction distribution is provided on FIG. 5 for over ten light oil/gas condensate samples based on lab gas chromatography and distillation results. As illustrated, all the samples have a maximum fraction at C1, which may be due to the nature of light oil, for example. The mole fraction then declines dramatically with increasing carbon number. However, another increase is observed at C5 until a secondary maximum may be achieved at C8. Then the mole fraction decreases towards a plateau of zero. The exponential increasing trend from C5 to C8 and exponential decreasing trend from C8 to C36+ may be observed in FIG. 6, which is a semi-log plot of FIG. 5. Based on these observations, a split exponential distribution function may be used as the mole fraction distribution function as follows:

$$z_i = \begin{cases} \sigma e^{-\tau_1(k-i)^{\alpha_1}}, i = 5, ..., k \\ \sigma e^{-\tau_2(i-k)^{\alpha_2}}, i = k, ..., 200 \end{cases} \quad (1)$$

In equation 1, $z_i$ is the mole fraction of component with carbon number i and k is the single carbon number with the local maximum mole fraction, which may vary for different fluid samples. For the group of reservoir fluid samples shown on FIGS. 5 and 6, k=8~13. $\sigma$, $\tau$, and $\alpha$ are parameters to be solved for certain samples, wherein $\sigma$ is a scaling parameter to tune a total mole fraction of C5 to C200 and $\tau$ and $\alpha$ are parameters to tune the increasing and decreasing trends (e.g., concavity of the curves). The subscripts 1 and 2 in equation 1 denote the increasing and decreasing regions, respectively. The subscript i represents the single carbon number.

In step 408, the mole fraction distribution function may be solved. The mole fraction distribution function may include one or more unknown parameters that may need to be solved to characterize the component mole fractions of a reservoir fluid. By way of example, equation 1 includes five unknown parameters ($\sigma$, $\tau_1$, $\tau_2$, $\alpha_1$, and $\alpha_2$) that need to be solved for before component mole fractions may be determined. One or more constraints may be used for determining the unknown parameters in the mole fraction distribution function. Five constraints may be needed for solving equation 1 as there are five unknown parameters. The basis of the constraints that may be used for the mole fraction distribution function may include, without limitation, mole balance, mass balance, the continuity nature of the functions, or combinations thereof. The constraints may also include theoretical assumptions, semi-empirical assumptions, or empirical assumptions. Thus, determining the unknown parameters may be a semi-empirical or empirical determination. Accordingly, in step 408, the mole fraction distribution function (e.g., equation 1) may be solved to determine the unknown parameters.

In step 410, the mole fraction distribution function may be used to determine component mole fractions of the reservoir fluid. The reservoir fluid may be considered a clean reservoir fluid as the component mole fractions determined in step 410 may be of the reservoir fluid without contamination. Without limitation, with the unknown parameters of the mole fraction distribution function known, the mole fraction distribution function may be used to determine the C1-C200 component. By way of example, the component mole fractions determined from the mole fraction distribution function may be a deplumped component concentration that includes mole distribution of components, including for plus fractions (C5+, C6+, etc.). Where equation 1 may be used, the mole fraction or $z_i$ (i=1 to 200) of the sample fluid may be obtained.

In step 412, the composition of the fluid sample may be determined. The fluid sample composition may be component mole fraction. The composition determined in step 412 may be the composition of the fluid sample. In other words, the composition may the composition of the reservoir fluid contaminated with the well fluid (e.g., drilling fluid). In contrast, the component mole fractions determined in step 410 are for the clean reservoir fluid without contaminants. In general, the composition of the fluid sample may be determined using the component mole fractions from step 410 and the fluid contamination ($\lambda 3$). By way of example, equation 2 below may be used to determine the composition of the fluid sample:

$$mi_{cont} = \frac{\lambda_3 mi_{mud} + (1-\lambda_3)mi_{clean}}{\sum_{i=1}^{200}(\lambda_3 mi_{mud} + (1-\lambda_3)mi_{clean})} \quad (2)$$

Wherein $\lambda 3$ is fluid contamination, $mi_{clean}$ is the mole fraction of component i for the reservoir fluid, $mi_{mud}$ is the mole fraction of component i in the mud filtrate, and i represents the single carbon number. For example, i may be an integer from 1 to 200.

In step 414, equation of state calculations may be performed to derive calculated fluid properties. The equation of state calculations may include equation of state flash calculations carried out over the component mole fractions of the fluid sample determined in step 410. Equation of state flash calculations may be used to derive the gas to oil ratio and dead oil density, among other fluid properties, of the fluid sample. Equation of state calculations may be used to derive the phase envelope and bubble point of the fluid sample, among other properties. To reduce the computational complexity of the equation of state calculations, the component mole fractions of the fluid sample may be lumped, for example, to C1, C2, . . . , C34, C35, and C36+ mole fractions. The calculated fluid properties determined by the equation of state flash calculations may include one or more of gas-to-oil ratio, dead oil density, bubble point, and/or phase envelope, for example. "Dead oil" typically refers to an oil at sufficiently low pressure that it contains substantially no dissolved gas or relatively thick oil that has lost its volatile components. Additional calculated fluid properties may include, without limitation, liquid mole fraction distribution, vapor mole fraction distribution, the density, molecular weight and mole volume for the liquid and vapor portion of the "live oil."

The equation of state calculations may be based on equation of state equations that represent the functional relationship between pressure, volume, and temperature of the fluid sample. Equations of states may be used to predict physical properties, such as macroscopic pressure-volumetemperature properties, including bubble point, dew point, phase envelope, viscosity, gas-to-oil ratio, density, combinations thereof.

Equation of state calculations may use information or properties such as temperature, pressure, and composition. For example, one simple equation of state is PV=nRT, known as the ideal gas law, where P=pressure, V=volume, n=moles, R=Ideal Gas Constant (also used for units conversion), and T=absolute temperature (Kelvin or Rankine). When the physical properties and composition of the reservoir fluid under a given set of conditions are known, the behavior of the reservoir fluid at other pressures and temperatures may be predicted. Equations of state that may be used may include, for example, expansions of the ideal gas law to account for individual molecular compositions. According to some embodiments, they are third order equations. Any of a variety of equations of state may be used. The equation of state may be cubic or non-cubic. The equation of state may vary depending on one or more compositional components of the fluid sample. The equations of state have many names, as they have been modified to improve the match between predicted and observed behavior. Without limitation, the equation of state may be selected from ono or more of Boyle, Van der Waals, Redlich-Kwong, Soave-Redlich-Kwong, Peng-Robinson, Peng-Robinson-Stryjek-Vera, Patek-Tej a, Schmit-Wenzel, or Esmaeilzadeh-Roshanfekr.

A method that seeks to compute the contamination using the equation of state approach at various pumpout times simultaneously may be useful to an operator in the field. The method may assume that the formation and filtrate fluids are the same at all pumpout points. The mud composition may be represented as a Gaussian distribution with mean and standard deviation as the unknowns. FIG. 5 illustrates a Gaussian distribution representation of the mud using various numbers of pumpout data and the original mud is also shown for reference in the chart of FIG. 5.

Preliminary results shows knowing the density (or compressibility) of a mud filtrate may be important when mud composition may be represented by a Gaussian distribution. As an example, in FIG. 6, a synthetic case was examined where mud filtrate represented by Gaussian distribution and an algorithm was solved for pumpout data at eight locations. In examples, the algorithm may be an equation of state wherein the computed fluid properties, such as gas oil ratio, density, and compressibility, are minimized by a nonlinear least square optimization. The accuracy of the predicted contamination level with this new developed algorithm may be nearly the same as when an original mud composition may be used, as shown in the FIG. 6.

The proposed method applies a Gaussian distribution method to describe oil based mud (OBM) and use equation of state to estimate contamination at several times during pumpout. The Gaussian distribution may make it possible to predict consistent estimation of contamination with time. The technique may be applicable at real time or when all data has been collected to prepare final report.

The Cubic Equation of State (EOS), e.g., referring to FIG. 4 and step 414, utilizes a fluid composition to predict bulk physical properties for that as a function of temperature, pressure and volume. Different mixtures of fluids with different compositions behave differently. Therefore a mud filtrate fluid may be expected to behave differently than that of petroleum. The physical properties of the mixture may be dependent on the composition of each independent endmember. By analyzing both the composition and physical properties of different fractions of the mixture (even if the mixture fraction may be unknown), the properties of the individual endmembers (i.e. filtrate and the petroleum reservoir fluid) may be derived and in turn, the fraction of filtrate and petroleum derived. Also by utilizing multiple points in the derivation of filtrate fraction in a petroleum sample, noise or spikes in physical or compositional measurements may be smoothed out. The multipoint EOS contamination method involves simultaneously computing the contamination of reservoir fluid sample at the same depth but at different pumpout time. Unlike the current methods for estimating contamination that may rely on trend fitting, the EOS contamination method uses equation of states, formation fluids' inherent geochemistry and empirical correlations. Therefore, the EOS contamination method does not suffer from many shortcomings of the traditional trend fitting based methods such as tool drifting and dependence of end member filtrate. However, the EOS contamination method uses least square optimization method and spiky or non-smooth data usually result in convergence problems-non-convergence/false local convergence/slow convergence. EOS contamination results may be heavily dependent on the quality of data from which the EOS may be calculated. Conventional smoothing/despiking algorithm may removes some of the spikes but the trend in the data sometimes exhibits some oscillations (artifacts from smoothing and averaging the spikes and noise), sometimes leading to local convergence problem.

Issues with EOS calculations may be improved by a principal component analysis. A Principal Component Analysis (PCA) may be defined as an algorithm to condition low quality compositional and physical data for EOS filtrate contamination analysis in a petroleum sample. The PCA may be a method of reconstructing the optical spectral data from truncated PCA scores and loading to give smooth and well behaved data for fluid composition prediction and contamination estimation. The PCA reduces high dimensional dataset to orthogonal low dimensional set of features that capture information from the original dataset with minimal loss to information. In examples, the PCA may be an orthogonal transformation wherein the first few dimensions capture a portion of the information. The information not captured may be the sum of the eigenvalues of the dimensions that are not included in the model. PCA decomposes the original high dimensional dataset, X into two matrices V and U. Where V is the loading matrix and U is the scores matrix. Mathematically, the PCA decomposition may be represented as seen below:

$$X = U * VT \tag{3}$$

Figure 7:
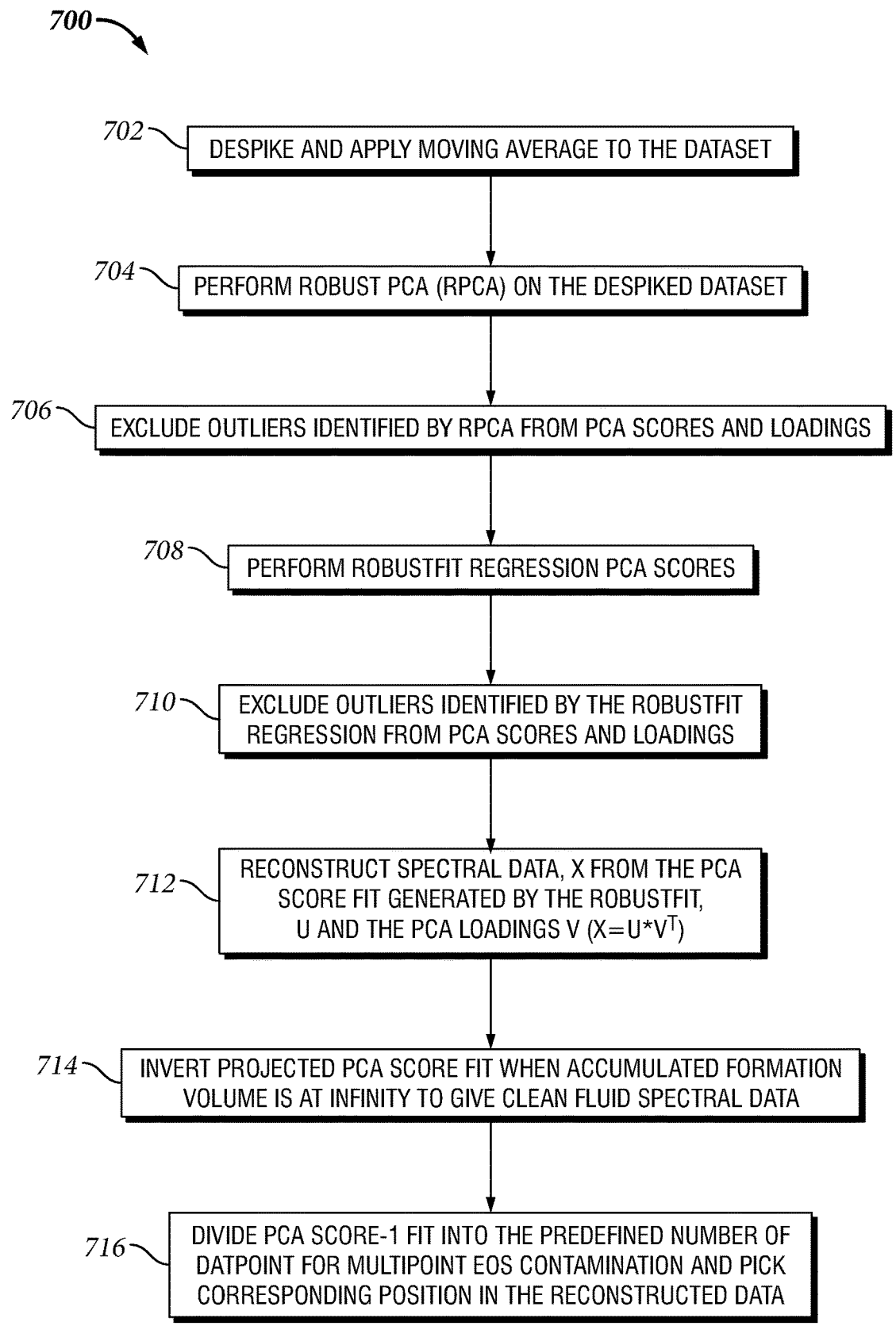
FIG. 7 is a chart illustrating density versus formation fluid accumulated volume.
Figure 8:
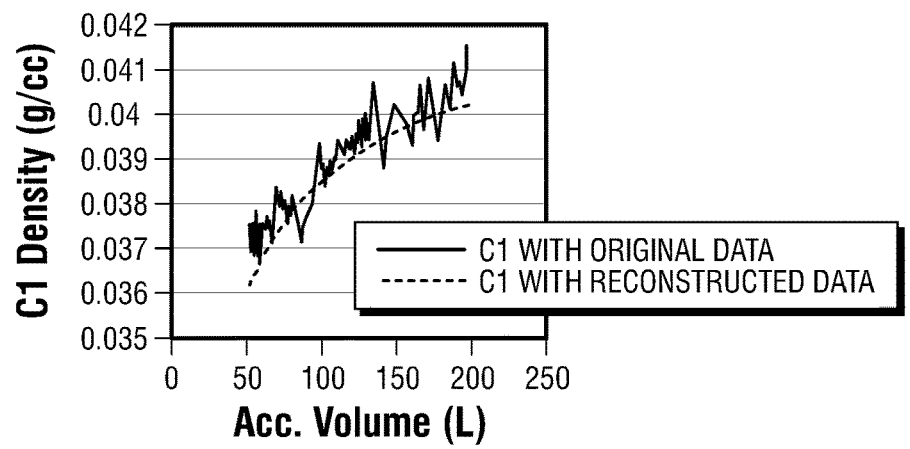
FIG. 8 is another chart illustrating density versus formation fluid accumulated volume.
Figure 9:
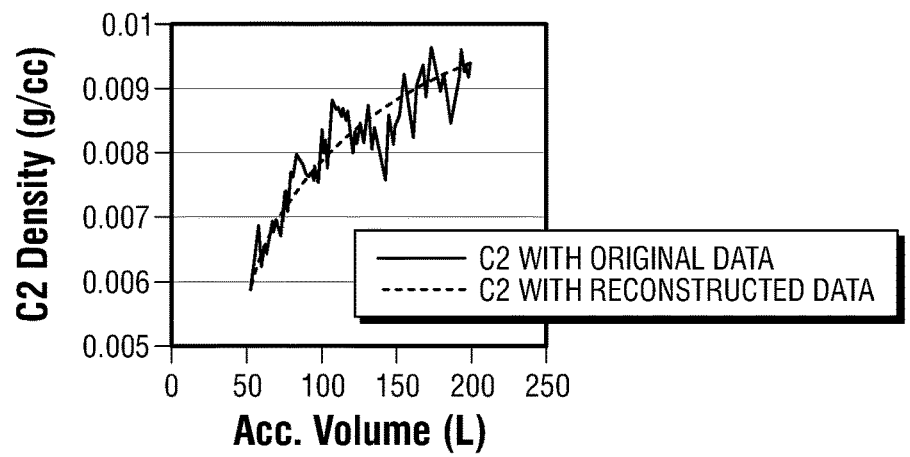
FIG. 9 is another chart illustrating density versus formation fluid accumulated volume.
Figure 10:
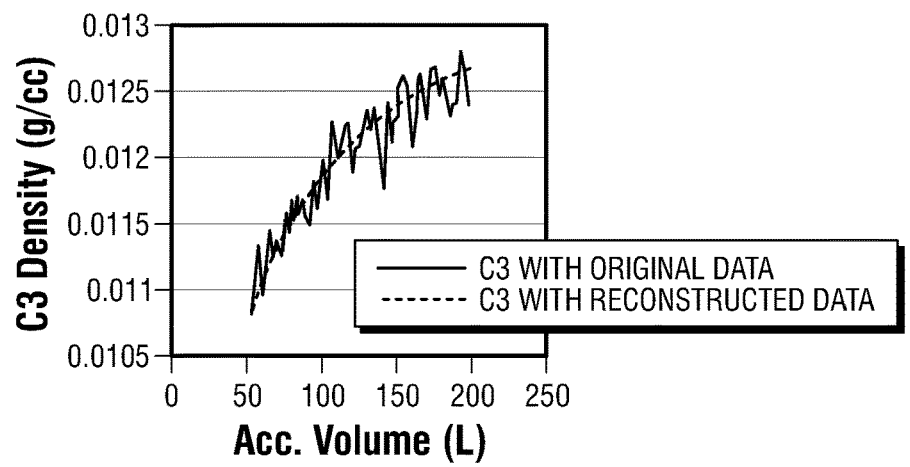
FIG. 10 is another chart illustrating density versus formation fluid accumulated volume.
Figure 11:
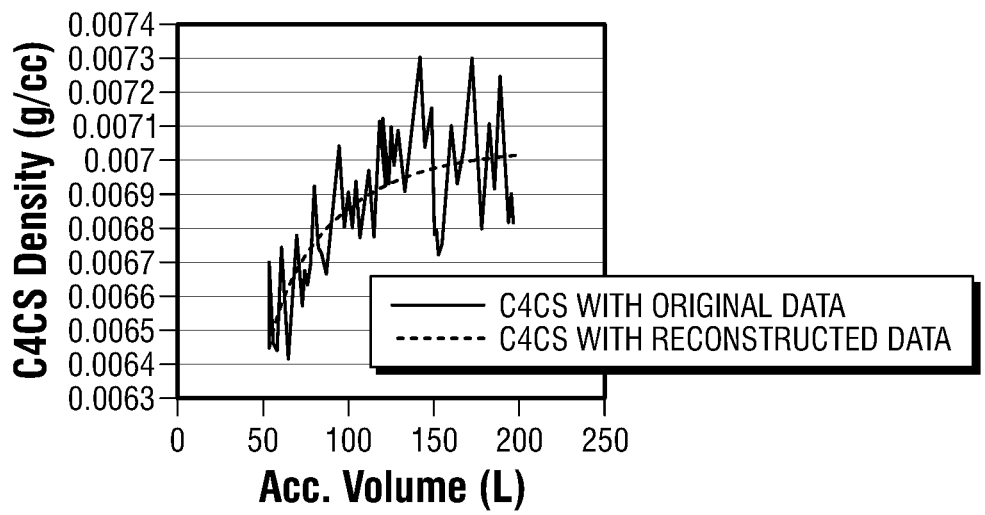
FIG. 11 illustrates an input to output flow chart.
Figure 12:
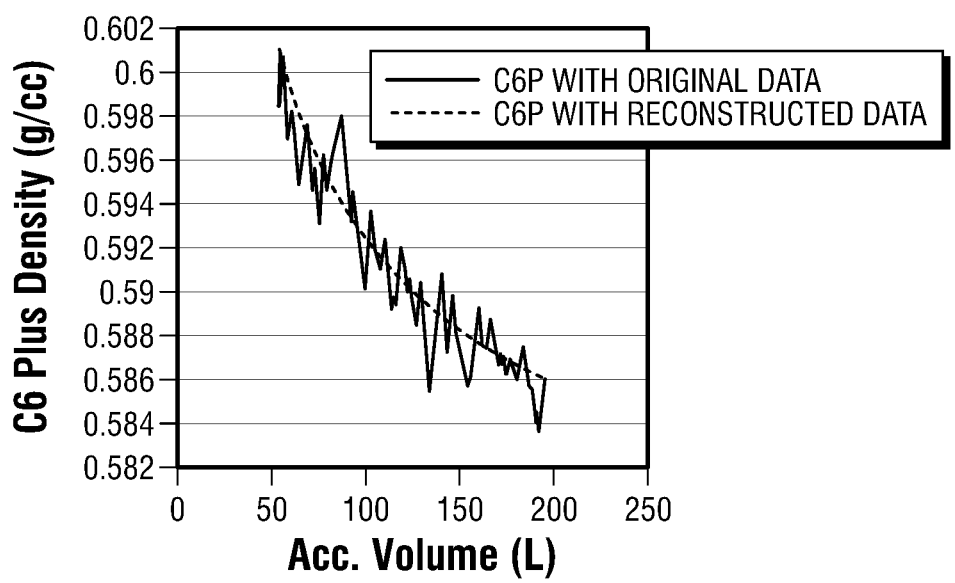
FIG. 12 illustrates a simulator that may produce real time contamination estimation.

The PCA score may be transformed variable values corresponding to a particular data point while PCA loading is the weights of each original variable when calculating principal components. FIG. 7 illustrates a workflow 700 for reconstructing optical spectral data from the PCA data. Workflow 700 may begin with the first step 702 to despike and apply a moving average to a data set of optical spectral data. Without limitations, despiking may be defined as the removal of spikes from data by applying a smooth function over a number of data points in the region where a spike occurs. A Hampel filter and a method of moving window averaging may be used to despike the data set. In step 704, the operator may perform a robust principal component analysis (RPCA) on the despiked data set. Unlike the classical PCA, RPCA is resistant to outliers in the data set.

Thus, in step 706, the operator may exclude outliers identified by the RPCA from PCA scores and loadings. In step 708 the operator may then perform robustfit regression PCA scores. The robustfit regression method is applied to the PCA scores where the independence variable of the robustfit may be the inverse of accumulated volume of formation fluid pumped out raised to the power density decay rate. The value of the density decay rate may be obtained by performing an optimization on the density dataset using a nonlinear constrained optimization method. Similar to RPCA, robustfit may be less sensitive to outliers in the dataset.

In step 710, the operator may exclude the outliers identified by the robustfit regression from PCA scores and loadings. The fit to the PCA scores generated by the robustfit regression method may be used in reconstructing the original data set data. For example, in step 712, the operator may reconstruct spectral data, X from PCA score fit generated by the robustfit, U and the PCA loadings V in the equation below:

$$X = U * V^T \qquad (4)$$

In step 714, the operator may invert projected PCA score fits when accumulated formation volume is at infinity to give clean fluid spectral data. The reconstructed data set is used to compute the fluid composition using any suitable machine learning algorithm. In step 716, the operator may divide PCA score−1 fit into the predefined number of data points for multipoint EOS contamination and pick corresponding position in the reconstructed data. The fluid composition computed using the PCA reconstructed spectral data gives smooth data that may be used for use in the EOS contamination estimation method using the least square optimization method.

FIGS. 8 to 12 shows the difference between the fluid composition computed using the original spectral data and the PCA reconstructed data for a particular formation fluid pumpout. In addition to providing smooth data for EOS contamination estimation, the projected value of the robust linear regression fit to the PCA scores when the accumulated volume of the formation fluid may be at infinity may be inverted to produce the clean fluid spectral data. Using the clean fluid spectral data, an operator may be able to accurately estimate the clean fluid composition using Neural Network predictive model. Additionally, the PCA score−1 is known to contain most of the information from the original dataset. The pumpout position for the multipoint EOS contamination may be automated dividing the PCA score−1 into the number of desired data points to be used for the multipoint EOS contamination. The corresponding position in the reconstructed data set may then be selected as a position where the contamination may be computed.

Referring back to FIG. 4, in step 416, the calculated fluid properties may be compared to the input fluid parameters. As described above, the input fluid parameters may be derived from analysis of the fluid sample in step 404. By way of example, gas-to-oil ratio and live oil density may be measured. From the live oil density, the dead oil density may be determined. The calculated fluid properties may also include a calculated gas-to-oil ratio and a calculated dead oil density. Without limitation, this comparison may include comparing the calculated gas-to-oil ratio with the input gas-to-oil ratio obtained from fluid analysis in step 404. Without limitation, this comparison may further include comparing the calculated dead oil density, gas to oil ration and bubble point pressure with those from input data from fluid analysis in step 404.

A tolerance error may be used, step 418, to determine if another iteration through the mole fraction distribution function (steps 406-414), fluid sample composition determination (step 412), and the equation of state calculations (step 414) may be required. The tolerance error may be a small value selected to impact the iteration number and total calculation time, but should have minimal impact on the final results. Without limitation, if the relative differences between the input fluid parameters and the calculated fluid parameters are not within a tolerance error, then another iteration may be required. By way of example, if the relative difference between the calculated gas-to-oil ratio and input gas-to-oil ratio and between the calculated dead oil density and dead oil density derived from the input dead oil density, are not within a tolerance error, then another iteration may be required. If the tolerance error determines that another iteration may be required, the iterated values (e.g., molecular weight of $C_{6+}$ components ($\lambda 1$), density of $C_{36+}$ components ($\lambda 2$), and/or fluid contamination $\lambda 3$) may be updated (step 176) and steps 408 to 418 may be repeated. Updating values for the molecular weight of $C_{6+}$ components ($\lambda 1$), density of $C_{36+}$ components ($\lambda 2$), and/or fluid contamination ($\lambda 3$) may utilize any of a variety of different analysis algorithms, including, without limitation, Newton-Raphson method. The iteration of steps 408 to 418 may be repeated with values for the molecular weight of $C_{6+}$ components ($\lambda 1$), density of $C_{36+}$ components ($\lambda 2$), and fluid contamination ($\lambda 3$) obtained until values for the comparison of step 416 or within the tolerance error of step 418.

Figure 13:
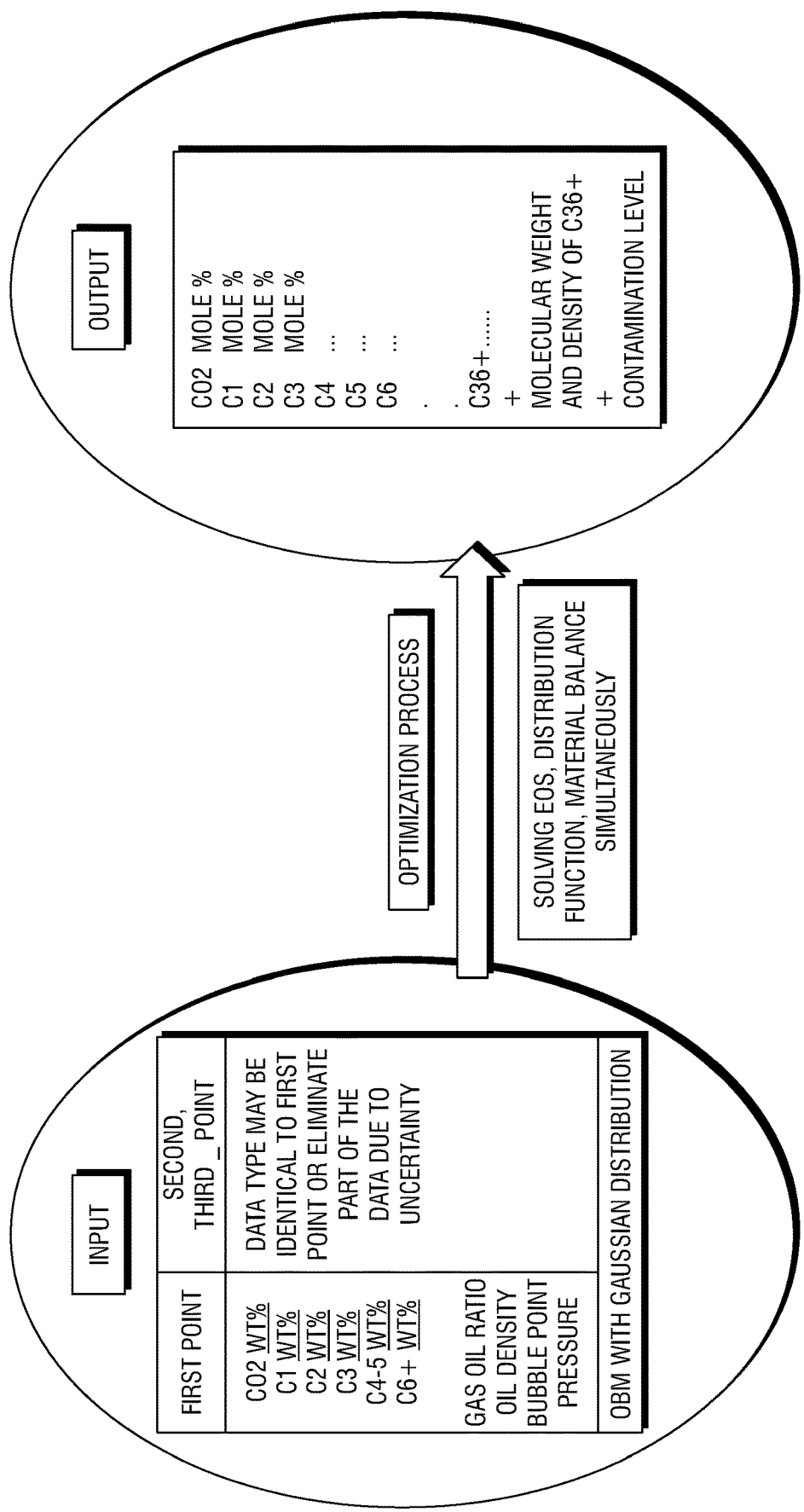

When the tolerance error of step 418 may be satisfied, method 400 may move to step 422 and optimized values for iterated parameters, including the molecular weight of $C_{6+}$ components ($\lambda 1$), density of $C_{36+}$ components ($\lambda 2$), and fluid contamination ($\lambda 3$) for the reservoir fluid may be returned. In step 424, the optimized values may result in optimized values may be used to generate an output of component mole fractions (e.g., C1-C200 mole distributions) and pressure-volume-temperature properties, such as bubble point and phase envelop prediction, among others, for the reservoir fluid. FIG. 13 illustrates a simulator which produces real time contamination estimation and optimized outputs described above. The output may also include the fluid contamination, which, may include for example, the drilling fluid contamination in the fluid sample of the reservoir fluid. Without limitation, the optimized values may be used to calculate the output values for component mole fractions (e.g., C1-C200 mole distributions) and pressure-volume-temperature properties. The component mole fractions may be a delumped component mole fractions. The delumped mole fractions may comprise component mole fractions for each carbon number from C1 to C200. Alternatively, the delumped component mole fractions may be expanded, but may continue to have some of the heavier hydrocarbons lumped into a group. For example, ten, twenty, thirty, or even more component mole fractions may be provided for C5+ hydrocarbons.

Existing contamination estimation methods currently being used rely on trend fitting. In examples, PCA data reconstruction may be used for making data smooth enough for EOS contamination methods. The methods using an EOS contamination method, described above, do not rely on any trend fitting that suffers from a number of shortcomings such as tool drifting, dependence of end members, sensitivity of the contamination prediction on data selected, and/or combinations thereof. Also, the inversion of the asymptotic PCA score allows us to estimate the clean formation fluid composition.

The method of using the spectral reconstructed data in predicting fluid composition of the EOS contamination method gives a reliable and viable means of using the EOS contamination method in estimating formation fluid contamination in real time. This allows us to estimate formation fluid contamination using a method that does not rely on data trend fitting. Also the estimation of the clean fluid composition may allow an operator to predict clean fluid composition in real time.

Distinctive improvements over current methods may be the ability to solve the equations at multiple points during pumpout and characterizing of oil based mud with Gaussian distribution function which in turn reduced the variety of input. This technique may make it possible to eliminate bad data or missing data point without having significant impact on the predicted result. In the previous method, oil based mud cull composition was needed and equations were also solved at single time of pumpout. Being in real time, it may not be possible to have full composition of oil based mud filtrate on the other hand, model prediction may not be consistent for data point at the later stage of pumpout, therefore running the model may be needed at each single point which may take time depending on the situation. The proposed method tackles both issue and predicts contamination as well as clean fluid composition with sufficient confidence and accuracy.

Additionally, the proposed methods constrain existing method, improve the prediction and add more flexibility in contamination estimation and clean fluid characterization, reduce the uncertainty caused by missing or bad data point. Without limitation, the proposed method may improve estimation of contamination and obtaining clean sample as fast as possible is one of the main challenge during wireline sampling. Better prediction of contamination may impact the cost of the operation significantly, specifically related to the phase of exploration and appraisal where time and cost may be crucial for viability of the project.

Specific improvements may be the use of a neural network to predict fluid composition from the PCA reconstructed data to estimate formation fluid contamination, the use of asymptotic value of the PCA score for estimating the clean formation fluid composition, and automating the multipoint EOS contamination position using PCA score-1. After determining and obtaining a clean reservoir fluid, well operations may be performed to remove contaminated reservoir fluid to allow for pumpout of the clean reservoir fluid from the wellbore.

The preceding description provides various embodiments of systems and methods of use which may contain different method steps and alternative combinations of components. It should be understood that, although individual embodiments may be discussed herein, the present disclosure covers all combinations of the disclosed embodiments, including, without limitation, the different component combinations, method step combinations, and properties of the system.

This method and system may include any of the various features of the compositions, methods, and system disclosed herein, including one or more of the following statements.

Statement 1. A method for determining fluid contamination may comprise monitoring a fluid sample, wherein the fluid sample comprises a reservoir fluid contaminated with a well fluid, and obtaining input parameters, wherein the input parameters comprise fluid properties obtained from measurement of the fluid sample and mud filtrate composition. The method may further comprise representing a mud composition as a Gaussian distribution, selecting a plurality of input data during a pumpout, determining calculated fluid properties of the reservoir fluid using an equation of state filtrate analysis, and repeating steps of determining component mole fractions and determining calculated fluid properties and further obtaining updated values of iterative parameters for use in a mole fraction distribution function until a comparison of one or more of the calculated fluid properties with one or more of the input parameters is within a tolerance error.

Statement 2. The method of statement 1, further comprising conditioning the equation of state filtrate analysis with a principal component analysis.

Statement 3. The method of statements 1 or 2, wherein the principal component analysis comprises despiking an original dataset, performing a robust principal component analysis on the original dataset to obtain a principal component analysis score, applying a robustfit regression to the principal component analysis score to obtain a reconstructed dataset, and computing a fluid composition form the reconstructed dataset.

Statement 4. The method of statements 1 to 3, wherein the despiking an original dataset is performed by a Hampel filter.

Statement 5. The method of statements 1 to 4, wherein the computing a fluid composition is performed by a Neural Network.

Statement 6. The method of statements 1 to 5, wherein the robustfit regression is an inverse of accumulated volume of a formation fluid pumped out raised to a power density decay rate.

Statement 7. The method of statements 1 to 6, further comprising removing the reservoir fluid based at least in part on the calculated fluid properties.

Statement 8. The method of statements 1 to 7, wherein obtaining the fluid sample comprising operating a downhole fluid sampling tool in a wellbore to obtain the fluid sample.

Statement 9. A spectral data reconstruction method may comprise despiking an original dataset of optical spectral data, applying a moving average to the original dataset to obtain a despiked dataset, performing a robust principal component analysis on the despiked dataset to identify a first set of outliers, excluding the first set of outliers from a principal component analysis score and a principal component analysis loading, performing robustfit regression on the principal component analysis score to obtain a second set of outliers, excluding the second set of outliers from the principal component analysis score and the principal component analysis loading to obtain a spectral data, reconstructing the spectral data, inverting the principal component analysis score, dividing the principal component analysis score for a predefined number of data points, identifying a location of a clean reservoir fluid in a subterranean formation penetrated by a wellbore, removing a contaminated reservoir fluid, and performing a pumpout to remove the clean reservoir fluid from the wellbore.

Statement 10. The method of statement 9, wherein the despiking the original dataset is performed by a Hampel filter.

Statement 11. The method of statements 9 or 10, wherein the reconstructing the spectral data is performed by an algorithm $X=U*V^T$, wherein X is reconstructed spectral data, U is the principal component analysis score, and V is the principal component analysis loading.

Statement 12. The method of statements 9 to 11, wherein inverting the principal component analysis is performed when accumulated formation volume is at infinity.

Statement 13. The method of statements 9 to 12, further comprising picking a corresponding position in the reconstructed data.

Statement 14. A system for determining fluid contamination may comprise a downhole fluid sampling tool operable to obtain fluid samples of a reservoir fluid contaminated with a well fluid while the downhole fluid sampling tool is disposed in a wellbore and a processing unit. The processing unit may be operable to (i) obtain input parameters, wherein the input parameters comprise fluid properties obtained from measurement of a fluid sample from the downhole fluid sampling tool and mud filtrate composition; (ii) represent a mud composition as a Gaussian distribution; (iii) select a plurality of input data during a pumpout; and (iv) determine calculated fluid properties of the reservoir fluid using an equation of state filtrate analysis.

Statement 15. The system of statement 14, wherein the operating unit is further operable to condition the equation of state filtrate analysis with a principal component analysis.

Statement 16. The system of statements 14 or 15, wherein the operating unit is further operable to despike an original dataset, perform a robust principal component analysis on the original dataset to obtain a principal component analysis score, apply a robustfit regression to the robust principal component analysis score to obtain a reconstructed dataset, and compute a fluid composition form the reconstructed dataset.

Statement 17. The system of statements 14 to 16, wherein the operating unit is further operable to despike an original dataset is performed by a Hampel filter.

Statement 18. The system of statements 14 to 17, wherein the robustfit regression is an inverse of accumulated volume of a formation fluid pumped out raised to a power density decay rate.

Statement 19. The system of statements 14 to 18, wherein the well fluid comprises a drilling fluid.

Statement 20. The system of statements 14 to 19, wherein the operating unit is further operable to obtain the fluid sample comprising operating a downhole fluid sampling tool in a wellbore to obtain the fluid sample.

It should be understood that the compositions and methods are described in terms of "comprising," "containing," or "including" various components or steps, the compositions and methods can also "consist essentially of" or "consist of" the various components and steps. Moreover, the indefinite articles "a" or "an," as used in the claims, are defined herein to mean one or more than one of the element that it introduces.

Therefore, the present embodiments are well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Although individual embodiments are discussed, the invention covers all combinations of all those embodiments. Furthermore, no limitations are intended to the details of construction or design herein shown, other than as described in the claims below. Also, the terms in the claims have their plain, ordinary meaning unless otherwise explicitly and clearly defined by the patentee. It is therefore evident that the particular illustrative embodiments disclosed above may be altered or modified and all such variations are considered within the scope and spirit of the present invention. If there is any conflict in the usages of a word or term in this specification and one or more patent(s) or other documents that may be incorporated herein by reference, the definitions that are consistent with this specification should be adopted.

What is claimed is:

1. A method for determining fluid contamination, comprising:
    obtaining a fluid sample, wherein the fluid sample comprises a reservoir fluid contaminated with a well fluid;
    using one or more optical sensors to obtain a measurement of the fluid sample, wherein the measurement comprises a petroleum compositional measurement, wherein the petroleum compositional measurement comprises one or more component mole fractions of the reservoir fluid, and wherein the petroleum compositional measurement comprises spectral data;
    obtaining input parameters, wherein the input parameters comprise fluid properties obtained from the measurement of the fluid sample and mud filtrate composition;
    representing a mud composition as a Gaussian distribution;
    selecting a plurality of input data during a pumpout;
    determining calculated fluid properties of the reservoir fluid based, at least in part, on the spectral data and an equation of state filtrate analysis;
    comparing the calculated fluid properties to the input parameters to determine if a tolerance criterion is met, wherein the tolerance criterion is a tolerance error; and
    generating an output if the tolerance criterion is met, wherein the output comprises the calculated fluid properties or an estimate of the fluid contamination.

2. The method of claim 1, further comprising conditioning the equation of state filtrate analysis with a principal component analysis.

3. The method of claim 2, wherein the principal component analysis comprises despiking an original dataset, performing a robust principal component analysis on the original dataset to obtain a principal component analysis score, applying a robustfit regression to the principal component analysis score to obtain a reconstructed dataset, and computing a fluid composition from the reconstructed dataset.

4. The method of claim 3, wherein the despiking an original dataset is performed by a Hampel filter.

5. The method of claim 3, wherein the computing a fluid composition is performed by a Neural Network.

6. The method of claim 3, further comprising using the principal component analysis score to estimate a clean formation fluid composition.

7. The method of claim 3, wherein the method further comprises: inverting the principal component analysis score to form an inverted asymptotic principal analysis score; and estimating one or more clean formation fluid compositions based, at least in part, on the inverted asymptotic principal analysis score.

8. The method of claim 1, further comprising removing the reservoir fluid based at least in part on the calculated fluid properties.

9. The method of claim 1, wherein obtaining the fluid sample comprises operating a downhole fluid sampling tool in a wellbore to obtain the fluid sample.

10. The method of claim 1, wherein the well fluid comprises a drilling fluid.

11. The system of claim 1, wherein the equation of state filtrate analysis further comprises a non-cubic equation of state.

12. A system for determining fluid contamination, comprising:
    a downhole fluid sampling tool operable to obtain a fluid sample of a reservoir fluid contaminated with a well fluid while the downhole fluid sampling tool is disposed in a wellbore; and a processing unit operable to (i) obtain a measurement of the fluid sample from one or more optical sensors, wherein the measurement is a petroleum compositional measurement, wherein the petroleum compositional measurement comprises one or more component mole fractions, and wherein the petroleum compositional measurement comprises spectral data (ii) obtain input parameters, wherein the input parameters comprise fluid properties obtained from the measurement of the fluid sample and mud filtrate composition; (iii) represent a mud composition as a Gaussian distribution; (iv) select a plurality of input data during a pumpout; and (v) determine calculated fluid properties of the reservoir fluid based, at least in part, the spectral data and an equation of state filtrate analysis.

13. The system of claim 12, wherein the processing unit is further operable to condition the equation of state filtrate analysis with a principal component analysis.

14. The system of claim 13, wherein the processing unit is further operable to despike an original dataset, perform a robust principal component analysis on the original dataset to obtain a principal component analysis score, apply a robustfit regression to the robust principal component analysis score to obtain a reconstructed dataset, and compute a fluid composition from the reconstructed dataset.

15. The system of claim 14, wherein the processing unit is further operable to despike an original dataset and where despiking is performed by a Hampel filter.

16. The system of claim 14, wherein computing the fluid composition is performed by a Neural Network.

17. The system of claim 14, wherein the processing unit is further operable to use the principal component analysis score, and wherein the principal component analysis score is used to estimate a clean formation fluid composition.

18. The system of claim 12, wherein the well fluid comprises a drilling fluid.

19. The system of claim 12, wherein the processing unit is further operable to obtain the fluid sample comprising operating a downhole fluid sampling tool in a wellbore to obtain the fluid sample.

20. The system of claim 12, wherein the processing unit is further operable to compare the calculated fluid properties to the input parameters to determine if a tolerance criterion is met, wherein the tolerance criterion is a tolerance error; and generate an output if the tolerance criterion is met, wherein the output comprises component mole fractions or the reservoir fluid or an estimate of the fluid contamination.

* * * * *